United States Patent
Kamiya et al.

(10) Patent No.: US 7,511,160 B2
(45) Date of Patent: Mar. 31, 2009

(54) LACTONE DERIVATIVE AND ITS MANUFACTURING METHOD

(75) Inventors: Masayuki Kamiya, Niiza (JP); Kiyohiko Tajima, Nagoya (JP); Eiji Furuya, Kawasaki (JP); Hideo Hattori, Nagoya (JP)

(73) Assignees: Toyota Jidosha Kabushiki Kaisha (JP); Genesis Research Institute, Inc. (JP)

( * ) Notice: Subject to any disclaimer, the term of this patent is extended or adjusted under 35 U.S.C. 154(b) by 525 days.

(21) Appl. No.: 11/225,175

(22) Filed: Sep. 14, 2005

(65) Prior Publication Data

US 2006/0058536 A1  Mar. 16, 2006

(30) Foreign Application Priority Data

Sep. 16, 2004 (JP) ............................. 2004-270577

(51) Int. Cl.
*C07D 305/12* (2006.01)
(52) U.S. Cl. ....................... 549/326; 549/323
(58) Field of Classification Search ................ 549/326, 549/323
See application file for complete search history.

(56) References Cited

FOREIGN PATENT DOCUMENTS

| JP | 62-36518 | 8/1987 |
|---|---|---|
| JP | 9-308497 | 12/1997 |
| JP | 2003-250592 | 9/2003 |

OTHER PUBLICATIONS

Chiacchio et al Tetra. 54 (1998) pp. 5695-5708.*
Wolfrom et al Chem. Abs. 44 no, 52050 (1950).*

* cited by examiner

*Primary Examiner*—Janet L. Andres
*Assistant Examiner*—Raymond Covington
(74) *Attorney, Agent, or Firm*—Finnegan, Henderson, Farabow, Garrett & Dunner, LLP

(57) ABSTRACT

A lactone derivative that is expressed by the following formula (I).

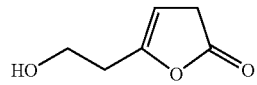

(I)

3 Claims, No Drawings

LACTONE DERIVATIVE AND ITS MANUFACTURING METHOD

BACKGROUND OF THE INVENTION

1. Field of the Invention

The present invention relates to a lactone derivative and its manufacturing method.

2. Description of the Related Art

Lactone derivatives, such as γ-lactone derivatives and δ-lactone derivatives, are useful when used as raw materials or intermediates in manufacturing medicinal chemicals, agricultural chemicals, polymers or the like. As disclosed in Japanese Patent Laid-open Application No. Hei 9-308497, there are various manufacturing methods for manufacturing these lactone derivatives that are characterized by using raw materials resulting from petroleum or other fossil fuel as starting materials.

On the other hand, biomass resources represented by waste, sludge, residue or the like resulting from biological resources, such as forest resources, aquatic resources, forest residues, aquatic residues, and agricultural residues, are prospective resources as they can be used as energy sources or other various resources. The biomass resources are organic substances resulting, for example, from plants or animals, and accordingly include a wide variety of types.

Fossil fuels are a big burden on the global environment and are not easy to handle with respect to disposal. If the present energy sources or raw materials used in chemical industries, which are originated from fossil fuel, can be replaced with biomass resources, it will be effective in reducing the burden that society as a whole places on the environments. In this respect, it is greatly expected that biomass resources will become, at least partly, energy sources or raw materials alternative to fossil fuel.

Among these biomass resources, hexose is a representative biomass resource resulting from the plants. Hexose is a monosaccharide having the widest distribution in the kingdom of animals and plants. In this respect, if hexose and its derivatives can be converted, as a biomass resource, into raw materials usable in chemical industries, hexose and its derivatives will be utilized as raw materials alternative to fossil fuel.

SUMMARY OF THE INVENTION

The present invention provides a novel lactone derivative and its manufacturing method.

The lactone derivative according to the present invention has the following structural formula (I).

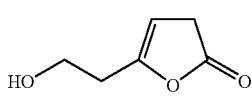
(I)

The present invention can provide a novel lactone derivative.

Furthermore, the present invention provides a method for manufacturing the lactone derivative. The above-described lactone derivative is at least one of the compounds expressed by the following structural formulas (I) and (II).

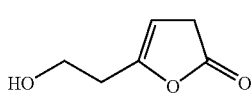
(I)

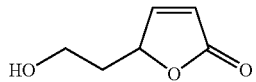
(II)

The above-described lactone derivative can be manufactured by causing a reaction of 2-deoxy-aldohexose in sulfuric acid.

The present invention can provide a method for manufacturing a novel lactone derivative by causing, in sulfuric acid, a reaction of 2-deoxy-aldohexose that is a derivative of hexose used as a starting raw material.

The above and other objects, features and advantages of the present invention will become more apparent from the following detailed description of an exemplary embodiment.

DETAILED DESCRIPTION OF THE INVENTION

One preferred embodiment of the present invention will be described in the following.

A lactone derivative according to one embodiment of the present invention has the following structural formula (I).

(I)

Furthermore, it is preferable that the above lactone derivative is manufactured by using 2-deoxy-aldohexose as a starting raw material.

For example, the 2-deoxy-aldohexose used as starting raw material can be selected from the group consisting of 2-deoxy-D-glucose, 2-deoxy-L-glucose, 2-deoxy-D-mannose, 2-deoxy-L-mannose, 2-deoxy-D-talose, 2-deoxy-L-talose, 2-deoxy-D-galactose, 2-deoxy-L-galactose, 2-deoxy-D-altrose, 2-deoxy-L-altrose, 2-deoxy-D-gulose, 2-deoxy-L-gulose, 2-deoxy-D-idose, 2-deoxy-L-idose, 2-deoxy-D-allose, and 2-deoxy-L-allose.

These 2-deoxy-aldohexoses may have a ring isomeric structure, such as a pyranose ring structure or a furanose ring structure. In this case, regarding the isomeric structure of these materials, either α-type or β-type or a combination of these types can be accepted.

These 2-deoxy-aldohexoses can be manufactured from corresponding aldohexoses acting as starting substances by using conventional methods such as a fermentation process.

Furthermore, it is preferable that the above-described lactone derivative is manufactured by causing a reaction of 2-deoxy-aldohexose in sulfuric acid.

The concentration of sulfuric acid used as solvent should be determined considering the reactivity of the selected 2-deoxy-aldohexose, although it is not limited to a specific value. The sulfuric acid used as solvent can be prepared by diluting a commercial concentrated sulfuric acid of about 90% to about 98% with tap water, ion exchange water, purified water, or the like so as to obtain a predetermined concentration.

In the reaction, the concentration of 2-deoxy-aldohexose relative to the sulfuric acid should be determined considering the solubility of selected 2-deoxy-aldohexose, although it is not limited to a specific value.

The reaction temperature should be set considering the reactivity of selected 2-deoxy-aldohexose, although it is not limited to a specific value. A preferable range of the reaction temperature is from about 10° C. to about 30° C. If the reaction temperature is less than about 10° C., the reaction will not advance smoothly. If the reaction temperature exceeds about 30° C., undesirable byproducts may be produced. However, in the event that the reaction does not advance smoothly, an appropriate heat treatment may be employed.

The reaction time should be determined considering the reactivity of selected 2-deoxy-aldohexose, although it is not limited to a specific value. Furthermore, the reaction time should not be extended unnecessarily.

Once the reaction of 2-deoxy-aldohexose that acts as starting raw material is finished by using a predetermined concentration of sulfuric acid and setting a predetermined concentration of starting raw material relative to the sulfuric acid, at a predetermined reaction temperature, and for a predetermined reaction time, a reaction product can be separated from the solvent by using a conventional method. For example, after the reaction solution is diluted with water to cause deposition of the reaction product, the reaction product can be separated using a filtering process, such as filtration under reduced pressure, filtration under increased pressure, or natural filtration, or by using a centrifugal separator. However, there may be cases where no deposit of reaction product is obtained after the reaction solution is diluted with water. In such a case, the reaction product can be separated by distillation or by using an evaporator or other comparable method for removing the solvent. Furthermore, the same method for removing the solvent, such as distillation or use of an evaporator, can be used when the reaction product is removed directly without diluting the reaction solution with water.

Before starting the process of separating the reaction product, it is preferable to neutralize the reaction solution with alkali, such as calcium carbonate, sodium carbonate, potassium carbonate, sodium hydrogen carbonate, calcium hydroxide, sodium hydroxide, potassium hydroxide, or ammonia water. Furthermore, a neutralization reaction caused by alkali is desirable if it can realize weak acidic conditions in the range of pH=about 3 to about 7, preferably in the range of pH=about 3 to about 6, so that the reaction product can be smoothly separated from the salt produced as a result of the neutralization reaction. If the pH value exceeds about 7, the alkali added to cause a neutralization reaction will assist formation of a salt of the reaction product. Thus, it will be difficult to separate the reaction product from the salt resulting from the neutralization reaction, such as calcium sulfate, sodium sulfate, or potassium sulfate. Furthermore, if the pH value is less than about 3, strong acidity will cause problems, for example, in preventing corrosion of the device or in performing the process of separation.

After the reaction product is separated from the solvent, it is preferable to wash the reaction product, if it is crystal, by using water such as tap water, ion exchange water, or purified water or by using alcohol, such as methanol or ethanol.

After the reaction product is separated from the solvent, or after the reaction product is separated from the solvent and subsequently washed with the water, it is preferable to purify the reaction product using a conventional method. If the reaction product is crystal, recrystallization or reprecipitation can be used to purify the reaction product. Furthermore, in a case where the reaction product is oily, distillation can be used to purify the reaction product. Furthermore, purification is realized by using chromatography, such as column chromatography, liquid chromatography (LC) for dispensation, or thin-layer chromatography.

The reaction product having been obtained in this manner can be dried using a conventional method. For example, drying under reduced pressure, drying by blowing, drying by heating, or natural drying can be used.

The following path is intended to show a procedure for producing the lactone derivative of this embodiment.

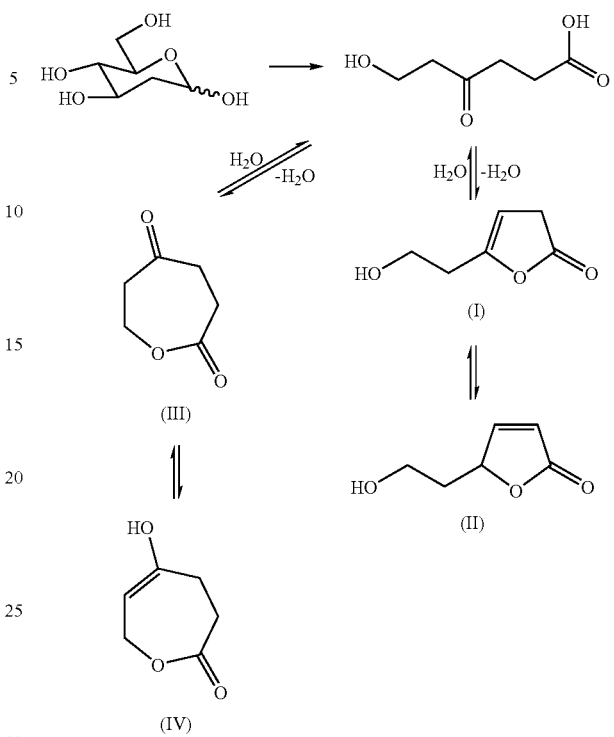

The lactone derivative produced according to this embodiment may be obtained, depending on isolation conditions, as a structure having the above-described structural formula (II) that is an isomer of the above-described structural formula II). Furthermore, the lactone derivative produced according to this embodiment may be obtained as a mixture of a structure having the above-described structural formula (I) and a structure having the above-described structural formula (II). Furthermore, the lactone derivative produced according to this embodiment may be obtained as a structure having the above-described structural formula (III) or (IV), or a combination of them.

In this manner, the manufacturing method of a lactone derivative according to this embodiment includes a reaction of 2-deoxy-aldohexose in sulfuric acid, thereby easily obtaining a novel lactone derivative that is useful as raw material or intermediate for manufacturing medicinal chemicals, agricultural chemicals, polymers or the like. The 2-deoxy-aldohexose, acting as starting raw material, uses saccharides. As saccharides are materials that are abundant in nature, the 2-deoxy-aldohexose is excellent as a raw material alternative to fossil fuel, from the point of view of being able to reduce the environmental impact.

EXAMPLES

Hereinafter, based on practical examples, the present invention will be explained in more detail, although the present invention is not limited to the following examples.

Example 1

First, 0.164 parts of 2-deoxy-D-glucose was added to 3.51 parts of 31.7% sulfuric acid in a glass reaction container and stirred together for one hour at 20° C. Then, after being diluted with 10 parts of ion exchange water, this mixture was subjected to a neutralization reaction caused by adding calcium carbonate. Then, by using a centrifugal separator, the calcium carbonate resulting from the neutralization was separated from the water solution. The water solution was then condensed, using an evaporator, to obtain 0.142 parts of a target object having the above-described structural formula (I) (yield: 75.6%).

The structure of this product was confirmed using an infrared spectrophotometer capable of measuring IR spectra of the product in the following manner.

IR (NaCl plate) [cm$^{-1}$]: 2678.04, 1792.0, 1748.2, 1446.4, 1369.2, 1224.6, 1169.1, 1048.6, 980.1, 907.8, 773.3, 732.8, 602.6, 523.6

Example 2

The example 2 is different from the above-described example 1 only in that 3.83 parts of 47.5% sulfuric acid was used as a solvent. A product resulting from the reaction was 0.0269 parts of the target object having the above-described structural formula (I) (yield: 14.3%).

Example 3

The example 3 is different from the above-described example 1 only in that 4.22 parts of 63.3% sulfuric acid was used as a solvent. A product resulting from the reaction was 0.0015 parts of the target object having the above-described structural formula (I) (yield: 0.8%).

While the present invention has been described with reference to an exemplary embodiment, it is to be understood that the invention is not limited to the disclosed exemplary embodiment. The scope of the following claims is to be accorded the broadest interpretation so as to encompass all modifications, equivalent structures and functions.

This application claims priority from earlier Japanese Patent Application No. 2004-270577 filed Sep. 16, 2004, which is hereby incorporated by reference herein in its entirety.

What is claimed is:

1. A method for manufacturing a lactone compound, wherein the lactone compound is at least one of the compounds expressed by the following structural formulas (I) and (II)

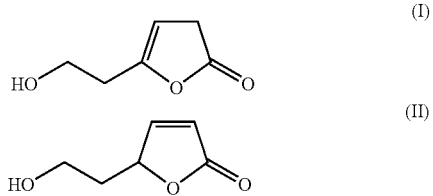

wherein the lactone compound is manufactured by reacting 2-deoxy-aldohexose with sulfuric acid.

2. The manufacturing method of a lactone compound according to claim 1, wherein a reaction temperature is in a range from about 10° C. to about 30° C.

3. The manufacturing method of a lactone compound according to claim 1, wherein the method further comprises subjecting a product resulting from the reaction of the 2-deoxy-aldohexose with the sulfuric acid to neutralization by alkali.

* * * * *